United States Patent
Lüchinger

(10) Patent No.: US 7,851,712 B2
(45) Date of Patent: *Dec. 14, 2010

(54) GRAVIMETRIC MOISTURE MEASUREMENT INSTRUMENT

(75) Inventor: Paul Lüchinger, Uster (CH)

(73) Assignee: Mettler-Toledo AG, Greifensee (CH)

( * ) Notice: Subject to any disclaimer, the term of this patent is extended or adjusted under 35 U.S.C. 154(b) by 401 days.

This patent is subject to a terminal disclaimer.

(21) Appl. No.: 11/738,202

(22) Filed: Apr. 20, 2007

(65) Prior Publication Data

US 2007/0256479 A1  Nov. 8, 2007

(30) Foreign Application Priority Data

Apr. 25, 2006  (EP)  ..................... 06113030

(51) Int. Cl.
*G10G 21/28* (2006.01)
*G01G 23/48* (2006.01)
*G01G 23/01* (2006.01)

(52) U.S. Cl. ............... 177/180; 177/50; 73/73; 73/76

(58) Field of Classification Search ............... 73/75–76, 73/73; 374/14; 177/50, 180–182, 262
See application file for complete search history.

(56) References Cited

U.S. PATENT DOCUMENTS

| | | | | |
|---|---|---|---|---|
| 2,849,676 A * | 8/1958 | Collins | ........................ | 324/695 |
| 3,618,368 A * | 11/1971 | Lesemann | ...................... | 73/73 |
| 3,890,825 A * | 6/1975 | Davis | .......................... | 374/14 |
| 4,106,329 A * | 8/1978 | Takahashi et al. | ............. | 374/14 |
| 4,291,775 A * | 9/1981 | Collins | ......................... | 374/14 |
| 4,465,152 A * | 8/1984 | Schmitter | ................... | 177/180 |
| 4,703,151 A * | 10/1987 | Sakamoto | .................. | 219/518 |
| 4,771,631 A * | 9/1988 | Lehtikoski et al. | ............. | 73/73 |
| 4,964,734 A | 10/1990 | Yoshida et al. | | |
| 5,211,252 A * | 5/1993 | Henderson et al. | ........ | 177/25.14 |
| 5,402,672 A * | 4/1995 | Bradford | ........................ | 73/76 |
| 5,485,684 A * | 1/1996 | Philipp et al. | .................. | 34/226 |
| 5,499,532 A * | 3/1996 | Kaiho et al. | .................... | 73/76 |
| 5,617,648 A * | 4/1997 | Leisinger et al. | .............. | 34/226 |
| 5,787,600 A * | 8/1998 | Leisinger et al. | ............... | 34/89 |
| 5,801,337 A | 9/1998 | Peake | | |
| 5,983,711 A * | 11/1999 | Pappas et al. | .................. | 73/76 |
| 6,227,041 B1 * | 5/2001 | Collins et al. | .................. | 73/76 |
| 6,255,603 B1 | 7/2001 | Spannagel et al. | | |
| 6,320,170 B1 * | 11/2001 | Jennings et al. | ............. | 219/679 |
| 6,675,636 B2 * | 1/2004 | Sadler | ........................... | 73/73 |
| 6,920,781 B2 * | 7/2005 | Olesen | ........................... | 73/73 |

(Continued)

FOREIGN PATENT DOCUMENTS

DE  4102233 A1 *  7/1992

(Continued)

*Primary Examiner*—David A. Rogers
(74) *Attorney, Agent, or Firm*—Standley Law Group LLP

(57) ABSTRACT

A measuring instrument for the gravimetric determination of moisture has a housing with a test compartment arranged in the housing, as well as a weighing device installed in the housing. The weighing device includes a sample receiver that is disposed inside the test compartment when in the measuring position. A radiation source arranged in the test compartment which during a test process serves to heat the sample placed on the sample receiver. A suction device, arranged adjacent to the test compartment, remove moisture and any other volatiles given off by the sample during the measurement process providing a more stable flow pattern in the test compartment.

22 Claims, 4 Drawing Sheets

U.S. PATENT DOCUMENTS

| | | |
|---|---|---|
| 7,145,086 B2 * | 12/2006 | Iiduka et al. ............... 177/180 |
| 7,148,455 B2 * | 12/2006 | Scalese et al. ............. 219/679 |
| 7,441,443 B2 * | 10/2008 | Diedrich et al. ............... 73/73 |
| 2001/0015293 A1 * | 8/2001 | Luchinger et al. ........... 177/184 |
| 2003/0188897 A1 * | 10/2003 | Ludi et al. ................. 177/145 |
| 2004/0104055 A1 * | 6/2004 | Nufer et al. ................ 177/180 |

FOREIGN PATENT DOCUMENTS

| | | | |
|---|---|---|---|
| DE | 19721124 A1 | * | 11/1998 |
| DE | 10123101 A1 | * | 11/2002 |
| EP | 1148329 A1 | | 10/2001 |
| FR | 2606510 A1 | | 5/1988 |
| GB | 2202054 A | | 3/1988 |
| JP | 09297095 A1 | * | 11/1997 |
| JP | 2000241328 A1 | * | 9/2000 |
| JP | 2001221440 A1 | * | 8/2001 |
| JP | 2003156423 A1 | * | 5/2003 |

* cited by examiner

GRAVIMETRIC MOISTURE MEASUREMENT INSTRUMENT

CROSS-REFERENCE TO RELATED APPLICATIONS

This application claims a right of priority under 35 USC §119 from European patent application 06 11 3030.8, filed 25 Apr. 2006, the content of which is incorporated by reference as if fully recited herein.

TECHNICAL FIELD

The present invention relates to a measuring instrument for the gravimetric determination of moisture content.

BACKGROUND OF THE ART

To determine the moisture content in a sample, the sample is dried and the weight of the sample is measured before and after the drying process. Due to the extensive amount of work involved, this method is very expensive as well as error-prone.

In some cases, the weight loss can also be measured during the drying process. In a given sample, the decrease in weight is a function of the temperature, the length of the drying time, and the conditions in the test compartment, and it conforms to a weight-versus-time curve which asymptotically approaches the dry weight of the sample. The curve for the given sample is determined by comparative experiments and can be expressed mathematically through an approximation formula. A measuring instrument for gravimetric moisture determination which is appropriately equipped with available electronic technology can compute the moisture content of a sample based on the measured parameters of the aforementioned curve and based on the length of the drying time and indicate the result on a display unit. With this method, the substance to be dried does no longer need to be totally desiccated; it is sufficient to determine the coordinates of two measurement points in the weight-versus-time diagram.

As has already been mentioned at the beginning, the weight change of a sample is substantially a function of the temperature, the length of the drying time, and the conditions in the test compartment. Especially the stringent requirements imposed on the test compartment are setting a limit to the accuracy of the commercially available instruments.

The term "test compartment" in the present context means a space which is enclosed by the housing of the measuring instrument and which can be opened in order to insert or remove a sample. Also arranged inside the test compartment are a sample receiver and a means to heat the sample. The sample receiver is connected to a gravimetric measuring instrument.

Normally, the sample is spread in a thin layer onto a flat sample receiver, for example a sample tray. For a uniform heating of the sample, the sample tray is preferably positioned so that its flat area is horizontal and parallel to the planar area occupied by the sample-heating means. As a means for heating the sample, a variety of radiation sources are used, such as heat radiators, microwave generators, halogen- and quartz lamps.

For a reliable drying process, it is necessary that the vapors coming out of the sample during the measuring process can be removed from the test compartment. It is therefore normal practice to arrange vent openings in the housing of the measuring instrument between the test compartment and the ambient environment of the measuring instrument. The vent openings which are arranged in the lower part of the test compartment serve as inlets for relatively dry and cool air. As the air is heated in the test compartment by the radiation source, it rises up inside the test compartment and is able in its heated state to absorb the moisture from the sample. The warm air that is charged with moisture leaves the test compartment through the vent openings that are arranged in the upper part of the test compartment.

A gravimetric moisture-determination instrument of the aforementioned type is disclosed in the U.S. Pat. No. 6,255,603 B1, issued to Spannagel on 3 Jul. 2001. The housing of this instrument has vent openings above the radiation source. These vent openings allow moisture from the sample to escape. Depending on the sample whose moisture content is to be determined, it is possible that as a result of the heating, other volatile substances are driven out of the sample, which may for example have a strong odor of their own or could be toxic or caustic. Such volatile substances can be produced in particular by a partial thermal decomposition of the sample. Furthermore, the moisture may not be limited to water that is distributed in the sample, but it is also possible that volatile substances whose boiling point is lower than the boiling point of water are driven out of the sample during the measuring process. This includes for example organic and inorganic solvents, gases that are occluded or dissolved in the sample, plasticizers that escape when testing plastic materials, and similar substances.

As mentioned above, warm air rises from the bottom to the top through the test compartment. Part of the rising air sweeps along the sample receiver and thereby causes a force acting against the direction of the load. Since this force depends to a large part on the velocity of the air flow in the test compartment, but as it also continuously changes due to the variable conditions in the test compartment, it is very difficult to compensate the error that this force causes in the weighing result. The drying rate also varies along with the air flow velocity, as the removal of the moisture escaping from the sample significantly affects the drying process.

Due to the errors in the time data which occur as a result, the accuracy that can be achieved in an analysis according to the mathematical model described above is limited. As an alternative to using the mathematical model, one can resort to the known method in which all of the moisture has to be driven out of the sample, at least to the extent that this is possible. However, this requires a very long drying time, whereby the risk is increased that a thermal decomposition or oxidation of the sample will occur as a result of the extended exposure to the heat from the radiation source.

For the reasons that have just been explained, it is hardly possible to determine an absolute value for the moisture content with a gravimetric moisture-determination instrument. For a more accurate determination of the moisture content of a substance, the Karl Fischer titration method is therefore still in use. This method is very labor-intensive, prone to user errors, and expensive.

It is therefore the object to provide in a gravimetric moisture-determination instrument of the kind mentioned in the introduction a test compartment with improved test conditions, in which the moisture content of a sample can be determined more precisely.

SUMMARY OF THE INVENTION

A gravimetric moisture-determination instrument that meets the foregoing objective comprises a housing, a test compartment arranged in the housing, and a weighing device installed in the housing. The weighing device includes a sample receiver which, in its measuring position, is located inside the test compartment. Also arranged in the test compartment is a radiation source for heating a sample placed on the sample receiver during a measuring process. In order to achieve more stable air-flow conditions in the test compartment, a suction device is arranged next to the test compartment, whereby the moisture and volatile substances escaping from the sample during the measurement process can be removed from the test compartment.

The term "measuring position" in the present context means that the elements arranged inside the measuring instrument are positioned in relation to each other in such a way that a measurement can be performed. In practice, this means that the sample receiver is positioned in the test compartment in the immediate vicinity of the radiation source and that closable openings for putting the sample into the test compartment are shut, so that the atmospheric flow conditions inside the test compartment are not influenced from the outside. The term "sample receiver" in essence means the load receiver or the weighing pan of a gravimetric measuring instrument.

The suction device slightly lowers the pressure level in the test compartment, whereby a gaseous medium is pulled in from outside the measuring instrument, for example through passages in the walls of the test compartment. The gaseous medium is channeled in an appropriate manner through the test compartment where it absorbs the moisture, whereupon it is removed from the test compartment through the suction device. In addition, the slight lowering of the pressure in the test compartment promotes the escape of the moisture from the sample. Of course, the gaseous medium can also be fed through the test compartment under an overpressure.

The suction device is not limited to systems such as for example an exhaust passage with a ventilator or a vacuum pump. If a gas delivery device introduces a gaseous medium under an overpressure from the outside into the test compartment, the gas delivery device and the exhaust opening for the removal of the gases from the test compartment likewise constitute a suction device.

Ideally, the weighing device and the test compartment are arranged side-by-side in the housing of the measuring instrument. At least one wall of the test compartment, preferably a wall that faces towards the weighing device, has at least one passage opening through which a connecting member reaches which connects the weighing device to the sample receiver that is arranged in the test compartment.

In one embodiment of the measuring device, the radiation source is arranged in the test compartment above the sample receiver, in relation to the direction of the load. The sample is thus heated from above.

The radiation source can be selected from a multitude of possibilities such as for example a heating plate, a heating foil, a halogen heat lamp, a quartz heat lamp, a heat radiator, a heat coil, a monochromatic light source, a Peltier element, or a microwave generator.

In a further embodiment of the measuring instrument, the radiation source includes a first radiation source and a second radiation source in an arrangement where the sample receiver is located between the first radiation source and the second radiation source. This arrangement has considerable advantages over the known state of the art. By arranging two radiation sources below and above the sample receiver, one gains significantly better control over the heat distribution. The sample is heated more uniformly and in a shorter time. The intensity of the radiation of both radiation sources can be matched appropriately to the sample and to the sample receiver that is being used. By choosing a suitable temperature profile across the thickness of the sample, the expulsion of moisture can additionally be speeded up without causing a breakdown or oxidation of the sample. The radiation source can be controlled or regulated by way of an electronic control- and regulation arrangement. To effect a regulation, it is necessary to measure the temperature of the sample and/or the inside temperature of the test compartment through suitable means, for example a temperature sensor arranged in the test compartment. For a more accurate determination of the test conditions, there can in addition be a humidity sensor arranged in the test compartment.

In spreading the sample over the sample receiver, it is unavoidable that the layer thickness will vary from place to place. The variations depend on the sample and the method of spreading. Due to the improved control over the heat distribution in the sample, the uneven spread of the sample on the sample receiver has less influence on the result of the measurement.

If the flow velocity of the gaseous medium is not too high, it is possible with an appropriate design of the test compartment to minimize turbulent flow in the gaseous medium and the harmful influence that it has on the measurement values. It is therefore preferred to arrange the suction device in relation to the load direction above the sample receiver and the radiation source. Thus, the suction device causes no additional turbulence of the gaseous medium in the test compartment.

To prevent the escaping moisture from being retained between the sample and the radiation source in a stagnant and moisture-saturated gas cushion which would impede the departure of the moisture from the measuring instrument, the radiation source is preferably equipped with openings allowing the gas to pass through.

Preferably, the measuring instrument is equipped with a calibration device which serves to calibrate the weighing device either on demand or automatically.

The calibration device can include one calibration weight or a plurality of calibration weights. In a particularly preferred embodiment, the center of mass of the one or more calibration weights during a calibration process lies on an axis that is oriented in the direction of the load and passes through the center of gravity of the sample receiver and/or of the sample. The purpose of this is to avoid eccentric load errors (also referred to as corner load errors) in the correction factor that is determined in the calibration process.

The weighing device of the measuring instrument includes a weighing cell which has a load-receiving portion and a stationary portion that is rigidly connected to the housing. To facilitate the operations of putting the sample into the test compartment and subsequently taking it out again, the sample receiver can be configured so that it can be coupled to and uncoupled from the load-receiving portion.

In order to minimize the extent to which the sample receiver is affected by the passing flow of gaseous medium, an interior draft shield which partially surrounds the sample receiver can additionally be arranged in the test compartment.

Although the test compartment is formed by a wall inside the housing and is thereby almost completely separated from the weighing device, the weighing results of the weighing device can be strongly influenced by the radiation sources. To provide thermal insulation, the wall of the test compartment is therefore preferably configured as a double wall at least between the test compartment and the weighing device, and the gaseous medium aspirated from outside the measuring instrument, preferably air, is directed to flow inside the double wall. The gaseous medium can, of course, also be introduced into the measuring instrument under overpressure. In the test compartment or inside the double wall there can in addition be a means to eliminate electrostatic charges, for example an ionizer, in order to eliminate electrostatic charges in the test compartment.

It is preferred if the gaseous medium is chemically stable and has a strong inertia against reacting with the sample and the materials of the test compartment. Gaseous media with these qualifications include for example protective gases such as nitrogen and noble gases such as argon.

In special cases, it is also possible to use a gaseous medium that reacts with the escaping vaporous or gaseous substances in order to counteract a re-absorption of the substances by the sample. In the case of water vapor, one can use for example a variety of halogens.

It is of advantage for special applications, if the gaseous medium has a predefined moisture content. This helps to improve the reproducibility of comparison measurements.

The weighing result is affected by currents moving through the test compartment, whether they are actively generated by means of a suction device or caused by purely thermal effects. The gaseous medium which rises from bottom to top in the test compartment pushes against the underside of the sample receiver and thereby lowers the measured weight of the sample. On the other hand, the lifting force on the sample due to buoyancy decreases with rising temperature. In the case of an actively generated current, the flow velocity in the vicinity of the sample receiver is known or can be determined through a measurement without a sample. Of course, effects of this kind can also be compensated electronically by determining a compensation value with a dummy sample prior to the actual measurement.

As has been described above, it is possible that in the drying process additional volatile substances are driven out of the sample, which can for example have a strong odor of their own or can have toxic or caustic properties. The suction device of the measuring instrument is therefore preferably equipped with a condenser in which the moisture and/or the volatile substances coming out of the sample are condensed out of the gaseous medium by cooling after the medium has left the test compartment. Instead of or in addition to the condenser, the suction device can have a chemical or mechanical filter. In a particularly preferred embodiment, the filter includes an adsorption agent, for example activated charcoal.

The afore-described embodiments of the measuring instrument allow a multitude of diverse processes to be carried out. One such process, which serves to determine the moisture content of a sample by measuring the weight loss over a predetermined test duration with a specified temperature profile, includes substantially the following steps:

conditioning of the test compartment to a prescribed temperature by means of at least one of the radiation sources and/or the suction device, placing the sample in the test compartment, determining the sample weight in predetermined time intervals, and/or continuously determining the weight loss over the entire duration of the test, and evaluating the measurement result and/or transmitting the measurement result to an indicating unit.

By conditioning the test compartment before starting the actual measurement, it is possible to achieve stationary conditions in the test compartment, which improves the reproducibility of the measurement results.

A further procedure can be performed with the measuring instrument if it is equipped with a system for conditioning the gaseous medium. This procedure serves to determine the affinity of the sample to moisture by measuring the weight gain over a predetermined test duration and under a prescribed temperature profile. The method includes substantially the following steps:

placing the sample in the test compartment, conditioning the sample to a predetermined moisture content, setting the test compartment to a predetermined temperature by means of at least one of the radiation sources and/or the suction device, injecting a gaseous medium into the test compartment with a known moisture content, at a predefined volume flow rate and a predefined temperature profile over the duration of the test period, determining the sample weight in predefined time intervals and/or determining the weight gain continuously over the entire duration of the test, and evaluating the measurement result and/or transmitting the measurement to an indicator unit.

As described above, the measurement result can be significantly influenced by the effects of atmospheric currents. As a means for largely eliminating these effects, a method suggests itself in which the determination of the sample weight occurs in predefined measuring intervals over the duration of the test, wherein the suction device is switched off before each measuring interval and switched back on after each measuring interval.

The preceding methods have in common that the test compartment is being conditioned. The conditioning phase is also the time for determining the correction for the errors due to buoyancy and atmospheric currents, if desired.

A first method for the electronic correction of an error due to buoyancy effects or atmospheric currents in the collected measurement results includes substantially the following steps:

placing a reference object into the test compartment, conditioning the test compartment to a specified temperature by means of at least one of the radiation sources and/or the suction device, determining the base weight value for the reference object, switching the suction device on, determining the correction weight values for the reference object in predetermined measurement intervals, and/or continuously measuring the weight change over the entire test duration, calculating the correction values or the correction profile over the entire test duration by subtracting the base weight value from the correction weight values, storing the correction values or the correction profile in a memory module, removing the reference object from the test compartment, and performing the measurements on the sample, taking into account the correction values determined in the preceding steps.

The reference body can be a dummy sample tray or also the actual sample tray on which the sample will be spread after the correction values have been determined.

A second method for electronically correcting an error due to buoyancy or atmospheric currents has substantially the following steps:

determining the volume flow rate or the mass flow rate of the gaseous medium by means of the suction device and/or by means of at least one sensor that is arranged in the test compartment, calculating the correction values or the correction profile over the entire test duration based on the results found for the volume flow rate or mass flow rate, storing the correction values or the correction profile in a memory module, and performing the measurements on the sample, taking into account the correction values determined in the preceding steps.

It is further possible to verify the results measured with the measuring device described above. The method for verifying the measurement values has substantially the following steps:

determining over the entire test duration the volume flow rate of the gaseous medium by means of the suction device and/or by means of at least one sensor that is arranged in the test compartment, by means of at least one humidity sensor, determining and registering over the entire test duration the humidity of the gaseous medium flowing into the test compartment, with said humidity either being kept constant or being allowed to vary, by means of at least one humidity sensor, determining and registering over the entire test duration the humidity of the gaseous medium flowing out of the test compartment, and calculating the verification values from the volume flow as determined above in this method as well as calculating the humidity difference between the incoming stream and the outgoing stream of the gaseous medium, over the entire duration of the test.

Due to the flow conditions and the inhomogeneous humidity distribution in the gaseous medium, these verification values tend to be less accurate than the weight loss data determined for the sample. They therefore serve, in essence, to verify that the measuring instrument is functioning properly.

BRIEF DESCRIPTION OF THE DRAWINGS

Details of the invention are presented in the description of the embodiments that are illustrated in the drawings, wherein.

DETAILED DESCRIPTION OF THE PREFERRED EMBODIMENTS

Figure 1:
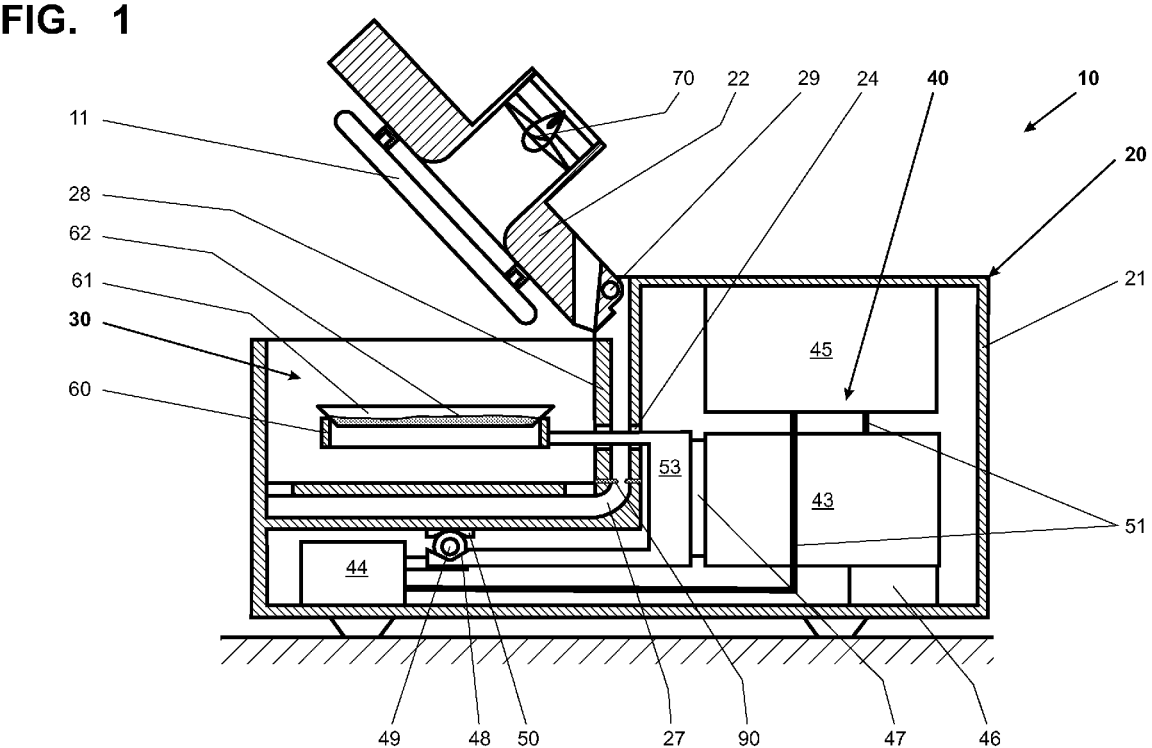
FIG. 1 is a cross-sectional view of a first embodiment of a measuring instrument.

FIG. 1, in a sectional view, illustrates a measuring instrument 10 in a first embodiment. The measuring instrument 10 has a housing 20 in which a test compartment 30 is arranged. The housing 20 is divided into a movable housing part 22 and a stationary housing part 21. Arranged in the stationary housing part 21 are a weighing cell 43, a calibration-weight-handling mechanism 44, and at least one electronic module 45, all of which are connected to each other by communicating means 51. The electronic module 45 contains at least one signal-processing module that is not shown in detail, and possibly also a control- and/or regulation module. The weighing cell 43 has at least a stationary portion 46 and a load-receiving portion 47. Known types of weighing cells are for example elastically deforming bodies carrying strain gauges, or weighing cells based on the principle of electromagnetic force compensation, or weighing cells with oscillating strings, capacitive weighing sensors and the like. The stationary portion 46 is rigidly connected to the stationary housing part 21. Arranged on the load-receiving portion 47 is a connecting member 53 which connects a sample receiver 60 to the load-receiving portion 47. As illustrated, a sample tray 61 with a sample 62 can be set on the sample receiver 60. With a suitable design of the sample receiver 60, one could of course also put the sample 62 directly on the sample receiver 60.

Further, a calibration weight receiver seat 48 is formed on the connecting member 53. A calibration weight 49 can be put on the weight receiver seat 48 by means of the calibration weight handling mechanism 44 actuated either by the user or under the control of the measuring instrument 10, in order to determine a correction value for the measuring signal based on the current operating condition of the measuring instrument 10. After the correction value has been determined, the calibration weight 49 is disconnected again from the calibration weight receiver seat 48 and held by the calibration weight handling mechanism 44 against a resting cradle 50 until the next calibration cycle takes place. Ideally, as a way to avoid eccentric load errors in the correction value, the mass center of the calibration weight 49 or—if applicable—the combined mass center of a plurality of calibration weights 49 lies close to an axis that passes through the center of gravity of the sample receiver 60 and/or of the sample tray 61 and/or the sample 62. The term "eccentric load error" (also referred to as corner load error) means the deviation that occurs in the weight measured by a weighing device for one and the same load when the latter is placed eccentrically on the sample receiver 60 in comparison to when it is put in a centered position.

As illustrated in FIG. 1, the movable housing part 22 is configured as a lid in which a radiation source 11 is arranged. A suction device 70 is incorporated above the radiation source 11 in the movable housing part 22. The movable housing part 22 is connected to the stationary housing part 21 through a hinge 29 which is located in the top of the housing 20, wherein the pivot axis of the hinge 29 runs substantially horizontal. The movable housing part 22 forms the upper part of the test compartment 30. FIG. 1 shows the measuring instrument 10 in the sample-loading position, i.e. the lid of the test compartment 30 is shown in the open position.

The lower part of the test compartment 30 is formed in the stationary housing part 21. The connecting member 53 which is mechanically connected to the weighing device 40 protrudes likewise into the lower part of the test compartment 30, so that the sample receiver 60 which is connected to the connecting member 53 is arranged entirely in the test compartment 30. To provide thermal insulation, a wall 28 of the stationary housing part 21 between the weighing device 40 and test compartment 30 is configured at least in part as a double wall. With the double-walled configuration of the wall 28, a ventilation duct 27 is formed through which a gaseous medium can be directed into the test compartment 30. The medium flowing through the duct during the measuring process cools the wall 28, so that the heat radiated from the test compartment cannot penetrate into the part of the housing that contains the weighing device 40.

Figure 2:
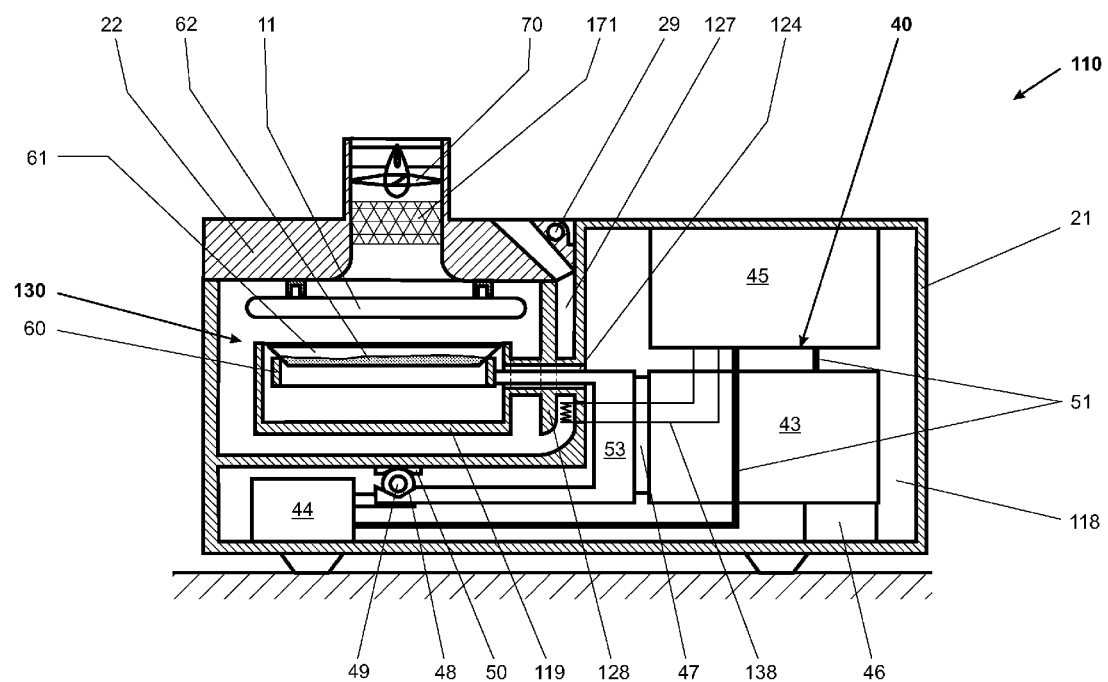
FIG. 2 is a cross-sectional view of a second embodiment measuring instrument.

There can further be various auxiliary device arranged in the ventilation duct 27. For example, the gaseous medium can be ionized by means of an ionizer 90 in order to eliminate electrostatic charges inside the test compartment 30. To allow the connecting member to protrude into the test compartment, the wall 28 has a passage opening 24. As shown in FIG. 2, this passage can also be configured as a closed tubular conduit, so that the medium streaming through the ventilation duct 27 cannot enter into the test compartment 30 through the passage 24 nor exert a force on the connecting member 53.

FIG. 2 shows a cross-sectional view of a second embodiment of the measuring instrument 110 according to the invention. The measuring instrument 110 itself is to a large extent analogous to the measuring instrument of FIG. 1. The same reference numerals are used for features that are identical, and the features are not described again in detail. In the test compartment 130 of the measuring instrument 110, which is shown in the closed condition in FIG. 2, an interior draft shield 119 is arranged which partially surrounds the sample receiver 60. Atmospheric currents of the gaseous medium can thereby be prevented from influencing the sample receiver 60. As already mentioned in the description of FIG. 1, the passage 24 is configured as a tubular conduit between the test compartment 130 and an interior space 118 of the stationary housing part 21 in which the weighing device 40 is arranged. The connecting member 53 reaches through this passage opening 124 and connects the sample receiver 60 to the load-receiving portion 47 of the weighing cell 43. Due to the design of the passage 124 as a tubular conduit across the ventilation duct 127, the intake stream of the gaseous medium flows around the passage 124 without coming into contact with the connecting member 53. As a result, none of the gaseous medium enters into the test compartment 130 directly through the passage 124. As shown, the tubular passage 124 further has the purpose to connect the interior draft shield 119 to the stationary housing part 21. As a means for preheating the gaseous medium before it enters into the test compartment 130, a ventilation-duct radiation source 138 can be arranged in the ventilation duct 127.

Figure 3:
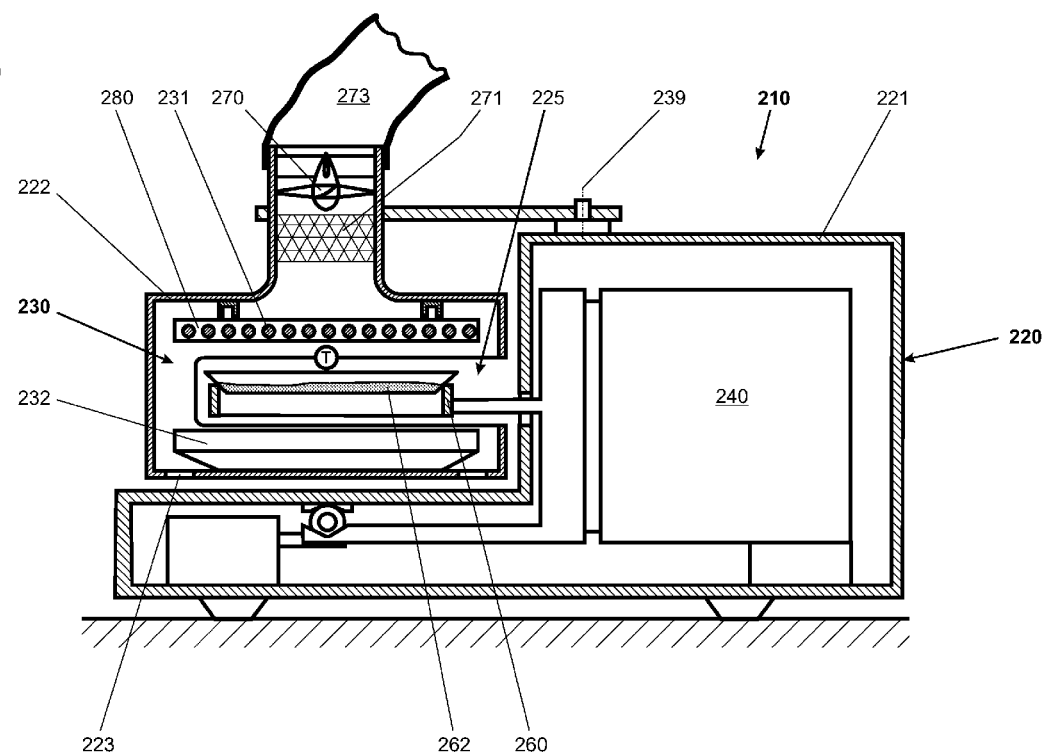
FIG. 3 is a cross-sectional view of a third embodiment measuring instrument.

FIG. 3 represents a cross-sectional view of the measuring instrument 210 in a third embodiment. A weighing device 240 arranged in the housing 220 has substantially the same elements as were named above in the description of FIG. 1 for the weighing device 40. The housing 220 is divided into a stationary housing part 221 and a movable housing part 222.

The weighing device 240 is largely enclosed by the stationary housing part 221. Only a sample receiver 260 which is connected to the weighing device 240 protrudes from the stationary housing part 221 and reaches into the space of the movable housing part 222 when the latter is set in position for performing measurements. Receptacles of different shapes such as sample trays 262, crucibles and the like can be placed on this sample receiver 260 which is ring-shaped in this example.

The movable housing part 222 forms the outer envelope of a unit which is pivotally connected to the stationary housing 221 so as to allow the movable housing part 222 to swivel about a vertical pivot axis 239. A test compartment 230 is formed in the interior of the movable housing part 222, with a first radiation source 231 in the upper part (relative to the load direction) of the test compartment 230 arranged substantially parallel to the sample receiver 260, in order to achieve as much as possible a homogeneous heat distribution at least on the surface of the sample 262. A second radiation source 232 below the sample receiver 260 in the lower part of the test compartment 230 is arranged substantially parallel to the sample receiver 260, with its radiation directed at the sample 262 from below. However, a parallel arrangement is not an absolute necessity. Depending on the sample 262 and the measurement to be performed, it may also be advantageous if the first radiation source 231 and/or the second radiation source 232 is arranged at an oblique angle relative to the sample receiver 260. Due to the two-sided exposure to the radiation from below and from above, a more homogeneous heat distribution is achieved in the sample 262. As a result, fewer local spots in the sample 262 become overheated, which could have the consequence of thermal decomposition or oxidation in the overheated spots of the sample 262. If the sample 262, for example in the form of a plastic material, has a relatively low melting point, the surface of the sample 262 can locally melt under excessively inhomogeneous heating, whereby the escape of moisture from the sample 262 is impeded. If a calculation method is used which involves time-dependent parameters, this can lead to massive errors in the result.

The movable housing part 222 further has a sample-loading opening 225 which is configured in such a way that the sample receiver 260 with the sample 262 in place does not touch the movable housing part 222 when the unit is swiveled. As shown in FIG. 3, in the measuring position of the apparatus the test compartment 230 encloses the sample receiver 260, with the first radiation source 231 arranged above the sample receiver 260 and the second radiation source 232 arranged below the sample receiver 260.

The first radiation source 231 is interrupted by a plurality of breakthrough openings 280 so as to form a grate, so that the moisture escaping from a sample 262 can be removed more easily from the vicinity of the sample 262 through the openings 280. A suction device 270 is built into the movable housing part 221 above the first radiation source 231. The suction device 270 lowers the pressure in the test compartment 230, so that for example the ambient air surrounding the measuring instrument 210 is drawn into the test compartment 230 through vent openings 223 or through the sample-loading opening of the movable housing part 221. The air taken in is heated in the test compartment 230 by the radiation sources 231, 232, absorbs the moisture escaping from the sample 262, and leaves the test compartment 230 by way of the suction device 270. The flow velocity of the aspirated gaseous medium which absorbs the moisture driven out of the sample 262 can be controlled by way of the suction power of the suction device 270. To deal with volatile substances which have for example a strong odor of their own, which are toxic or caustic, the suction channel of the suction device 270 can additionally be equipped with a condenser and/or a filter 271. Depending on the existing infrastructure, it is possible to send the gaseous medium with the absorbed moisture for example through a connecting hose 273 into the exhaust system of a fume-hood chamber.

Figure 4:
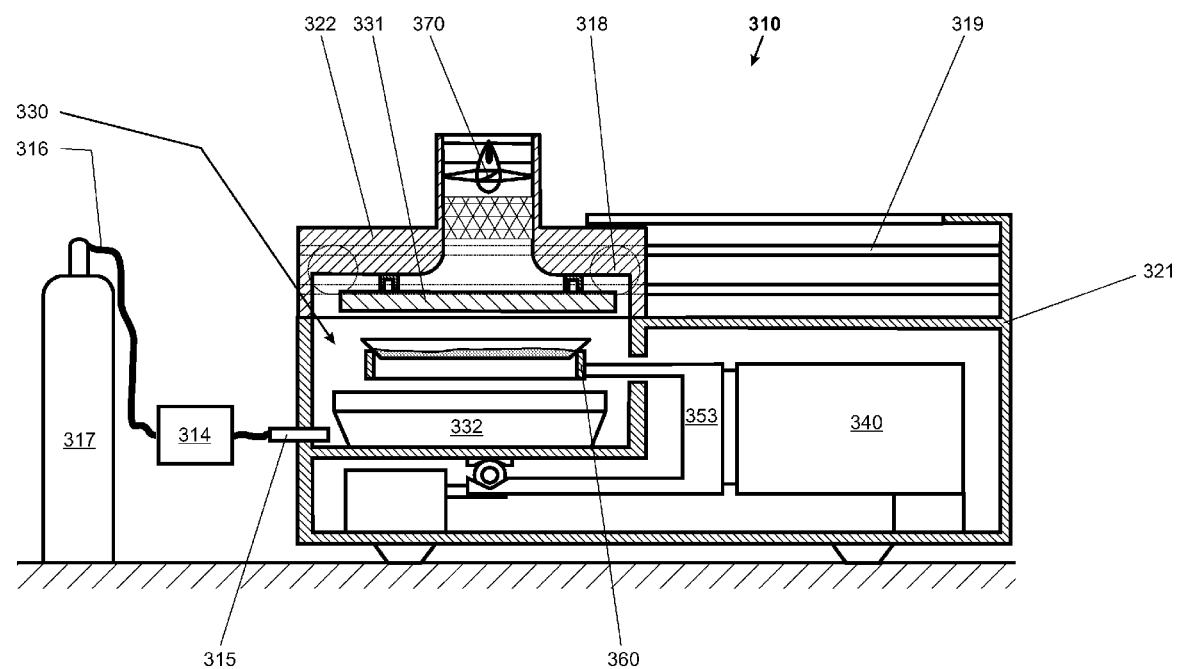
FIG. 4 is a cross-sectional representation of a fourth embodiment measuring instrument.

FIG. 4 shows a sectional view of the measuring instrument 310 in a fourth embodiment. The stationary housing part 321 and the elements arranged inside it, such as a weighing device 340, a sample receiver 360, as well as a connecting member 353, are substantially analogous to the elements which have been discussed above in the description of FIG. 1. Like the measuring instrument 210 of FIG. 3, the measuring instrument 310 has a first radiation source 331 and a second radiation source 332. The latter are positioned in the test compartment 330 in such a way that in relation to the load direction, the first radiation source 331 is arranged above the sample receiver 360 and the second radiation source 332 is arranged below the sample receiver 360.

The movable housing part 322 with the elements arranged in it, such as a first radiation source 331 and an integrally contained suction device 370, is substantially analogous to the movable housing part 22 of FIG. 1. However, unlike the arrangement in FIG. 1, the movable housing part 322 is not connected by a hinge to the stationary housing part 321, but is guided by means of rollers 318 and guide tracks 319 that allow linear movement of the movable housing part 322 in the stationary housing part 321. Instead of the ventilation channel 27, the test compartment 330 has a gas inlet port 315 which is connected by a flexible hose 316 to a pressurized container 317 or to a conduit system installed in the building. The pressurized container 317 stores a gaseous medium which is preferably conditioned by means of a conditioning device 314, so that when it enters the test compartment 330, the gaseous medium has a defined and constant moisture content. Since the gaseous medium flows into the test compartment 330 at an above-atmospheric pressure, the suction device 370 can also be replaced by vent outlet openings. The flow velocity through the test compartment 330 is in this case determined by the volume flow rate of the incoming stream of the gaseous medium at the nominal pressure in the test compartment 330 rather than by the suction power of a suction device 370.

The embodiments presented herein illustrate measuring instruments with different properties and features for the gravimetric determination of moisture content. For the sake of clarity, the different properties and features have been shown in different embodiments, but it is also possible to realize only one, or some, or all of the proposed features and properties in one measuring instrument.

What is claimed is:

1. A gravimetric measuring instrument for a sample, comprising:
   a housing,
   a test compartment arranged inside the housing and defined by a wall therewithin, at least a portion of which is a double wall that is configured to have a gaseous medium directed therethrough and into the test compartment, the wall of the test compartment having a passage opening therethrough;
   a weighing device installed in the housing in a side-by-side relationship relative to the test compartment, the weighing device comprising a sample receiver which is disposed inside the test compartment while performing a measurement;
   a connecting member, extending through the passage opening and connecting the weighing device to the sample receiver;
   a radiation source arranged in the test compartment and serving to heat the sample that is placed on the sample receiver during a measurement, and
   a suction device, arranged adjacent to the test compartment, for removing from the test compartment, in the gaseous medium, any moisture and/or volatile substances coming out of the sample during the measuring process.

2. The measuring instrument of claim 1, wherein:
   the radiation source comprises a first radiation source and a second radiation source, the sample receiver arranged between the respective radiation sources.

3. The measuring instrument of claim 1, wherein:
   the radiation source is provided with openings that allow gases to pass through.

4. The measuring instrument of claim 1, wherein:
   the weighing device further comprises a weighing cell with a load-receiving portion, the sample receiver being is configured to be selectively coupled to and uncoupled from the load-receiving portion.

5. The measuring instrument of claim 1, wherein:
   an interior draft shield, arranged in the test compartment, at least partially surrounds the sample receiver.

6. The measuring instrument of claim 1, wherein:
   the gaseous medium is chemically stable and/or chemically inert relative to both the sample and the materials of the test compartment.

7. The measuring instrument of claim 1, wherein:
   the gaseous medium has a known moisture content.

8. The measuring instrument of claim 1, wherein:
   the suction device is above the radiation source relative to a load direction of the weighing device.

9. The measuring instrument of claim 8, wherein:
   the radiation source is positioned above the sample receiver relative to the load direction.

10. The measuring instrument of claim 1, wherein:
    the weighing device further comprises a calibration device.

11. The measuring instrument of claim 10, wherein:
    the calibration device comprises one or more calibration weights, and
    a center of mass of the one or more calibration weights lies on an axis during a calibration process that is oriented in the load direction and passes through a center of gravity of at least one of: the sample receiver and the sample.

12. The measuring instrument of claim 1, further comprising:
    a means for eliminating electrostatic charges from the test compartment arranged in at least one of: the test compartment and the double wall.

13. The measuring instrument of claim 12, wherein:
    the electrostatic charge eliminating means comprises an ionizer.

14. The measuring instrument of claim 1, wherein:
    the suction device comprises at least one of: a condenser and a filter.

15. The measuring instrument of claim 14, further comprising:
    an adsorption agent in at least one of: the filter and the condenser.

16. A method for determining a moisture content of a sample using the measuring instrument of claim 1, the method comprising the steps of:
    setting the test compartment to a prescribed temperature using at least one of the radiation source and the suction device;
    placing the sample on the sample receiver in the test compartment;
    obtaining a measurement result by at least one of: determining the sample weight in predetermined time intervals, and determining a weight loss continuously over the test duration; and
    at least one of: evaluating the measurement result and transmitting the measurement result to an indicating unit.

17. The method of claim 16, wherein:
    in the measurement result obtaining step, the sample weight is determined at predetermined measurement intervals, with the suction device being turned off prior to the sample weight determination and turned on again after the sample weight determination.

18. A method for measuring a moisture affinity in a sample by measuring the weight increase in a test having a predetermined duration and with a defined temperature profile, using the measuring instrument of claim 1, the method comprising the steps of:
    placing the sample in the test compartment;
    conditioning the sample in the test compartment to a predetermined moisture content;
    setting the test compartment to a prescribed temperature using at least one of the radiation source and the suction device;
    injecting a gaseous medium with a known moisture content into the test compartment, at a predefined volume flow rate and a predefined temperature profile over the test duration;
    obtaining a measurement result by at least one of: determining the sample weight at predetermined measurement intervals and determining continuously the weight gain over the test duration of the test; and at least one of: evaluating the measurement result and transmitting the measurement result to an indicator unit.

19. The method of claim 18, wherein:

in the step of obtaining a measurement result, the sample weight is determined at predetermined measurement intervals, with the suction device being turned off prior to the sample weight determination and turned on again after the sample weight determination.

20. A method for correcting an error in the measurement value determined in the method of claim 16 or 18 due to buoyancy, comprising the steps of:

placing a reference object into the test compartment;

conditioning the test compartment to a pre-specified temperature using at least one of: the radiation source and the suction device;

determining a base weight value of the reference object with the suction device turned off;

switching the suction device on;

determining a set of correction weight values for the reference object for at least one of: measuring the weight at predetermined measurement intervals and measuring the weight change continuously over the test duration;

calculating, by subtracting the base weight value from the correction weight values, at least one of: the correction values and the correction profile over the test duration;

storing the calculated correction values and/or the correction profile in a memory module;

removing the reference object from the test compartment; and performing the measurement on the sample, taking into account the correction values.

21. A method for correcting an error in the measurement values determined in the measurement of claim 16 or 18 due to buoyancy, comprising the steps of:

determining at least one of a volume flow rate and a mass flow rate of the gaseous medium using at least one of the suction device and a sensor that is arranged in the test compartment;

calculating the correction values or the correction profile over the test duration based on the determined flow rate;

storing the correction values or the correction profile in a memory module; and performing the measurements on the sample, taking into account the correction values.

22. A method for verifying the results found through the methods of claim 16 or 18, comprising the steps of:

determining over the entire test duration the volume flow rate of the gaseous medium using at least one of: the suction device and a sensor that is arranged in the test compartment;

determining and registering over the test duration the humidity of the gaseous medium flowing into the test compartment, using a humidity sensor, with the humidity either being kept constant or being allowed to vary;

determining and registering over the test duration the humidity of the gaseous medium flowing out of the test compartment; using a humidity sensor; and calculating the verification values from the determined volume flow and the determined humidity difference between the incoming and outgoing gaseous medium streams over the test duration.

* * * * *